United States Patent [19]

Boren

[11] Patent Number: 4,869,240

[45] Date of Patent: Sep. 26, 1989

[54] CERVICAL TRACTION UNIT

[76] Inventor: John P. Boren, 15807 Hidden Cove, Houston, Tex. 77079

[21] Appl. No.: 219,891

[22] Filed: Jul. 14, 1988

Related U.S. Application Data

[63] Continuation of Ser. No. 922,204, Oct. 23, 1986, abandoned.

[51] Int. Cl.[4] ........................ A61H 1/02; A61F 5/24; A61F 5/04

[52] U.S. Cl. ........................ 128/75; 128/97.1; 128/81 B

[58] Field of Search ........................ 128/75, 87 B, 84 R, 128/69, 97; 24/500, 512, 494, 499; 269/254 CS, 237; 119/29

[56] References Cited

U.S. PATENT DOCUMENTS

| | | | |
|---|---|---|---|
| 1,347,913 | 7/1920 | Rink | 128/75 |
| 1,425,433 | 8/1922 | Zook | 128/75 |
| 2,232,414 | 2/1941 | Swann | 24/494 |
| 2,701,564 | 2/1955 | Wilhelm | 128/75 |
| 2,843,114 | 7/1958 | Hall | 128/75 |
| 2,932,112 | 4/1960 | Graves, Jr. | 43/42.02 |
| 3,403,675 | 10/1968 | Carr | 128/75 |
| 4,438,727 | 3/1984 | Thompson | 119/29 |

*Primary Examiner*—Robert A. Hafer
*Assistant Examiner*—Michael Brown
*Attorney, Agent, or Firm*—Dodge, Bush & Moseley

[57] ABSTRACT

An improved cerical traction apparatus adapted for use with an overhead door frame is disclosed. The traction apparatus has a spring mounted with a clamp. The spring is movable relative to the clamp between a rest position and an operating position for providing a range of traction loadings. A head halter or headstall for fastening to a user's head is mountable to a spreader bar secured to the spring.

When the traction apparatus is secured to the door frame, the user is quickly and conveniently able to achieve a range of loadings in the operating position or no loading in the rest position by the position of the headstall fastened to the user's head.

3 Claims, 1 Drawing Sheet

CERVICAL TRACTION UNIT

This application is a continuation, of application Ser. No. 922,204, filed 10/23/86 now abandoned.

BACKGROUND OF THE INVENTION

1. Field of the Invention

This invention relates generally to a cervical traction apparatus and, more particularly, to a cervical traction unit for use with an overhead door frame.

2. Description of the Prior Art

There are devices in common use for cervical traction. An example of a prior art device marketed by Graham - Field, Inc. of New Hyde Park, N.Y. 11040 is illustrated in FIG. 1. This device generally includes a bracket attached to a top of a door. In this device a cord is threaded through two pulleys spaced apart on the bracket. The end of the cord closest to the door is preferably secured to an empty plastic bag. The other end of the cord is secured to the center hole of a spreader bar.

The user then fastens on the head halter or headstall and sits on a chair facing the door in order to achieve the proper vector angle for traction of the user's cervical spine. The head halter is then attached to the spreader bar and, finally, water is added to the bag for desired weighting.

In addition to manufacturing expense, a problem with the above device is that the installation and use of the device is very difficult for the user. The user is not only required to add water while maintaining the securement of the head halter to the spreader bar but, if the user is required to place a range of traction loadings on the cervical spine for different time intervals, the water bag must be drained or filled to achieve the desired weighting. Additionally, water may leak from a punctured or torn plastic bag.

Another problem with the above device is that the user is required to face the door in order to achieve a prescribed traction angle as shown in FIG. 1. This limited viewing only makes a bad situation worse. It would be desirable if the user of the device could have enhanced viewing for watching children or television.

A clamp and spring, similar to the one used in the present invention, is used with a baby seat manufactured by Questor Juvenile Furniture Co. of Piqua, Ohio 45356. The baby seat is suspended from the spring which is clamped to an overhead door frame. This baby seat restrains the baby while allowing soothing jumping movement.

IDENTIFICATION OF OBJECTS OF THE INVENTION

An object of the invention is to provide an improved cervical traction unit.

It is another object of this invention to provide a cervical traction apparatus where a range of loadings can be quickly and conveniently achieved by simply positioning of the user's head fastened to the headstall.

It is another object of this invention to provide a cervical traction apparatus that enhances viewing by the user.

Another object of this invention is to provide a compact cervical traction apparatus that is easy to install and use yet is inexpensive to manufacture.

SUMMARY OF THE INVENTION

According to the invention, an improved cervical traction apparatus adapted for use with an overhead door frame is provided. The traction apparatus comprises a spring mounted with a clamp removably securable to the overhead door frame. The spring is movable relative to the clamp between a rest position and an operating position for providing a range of traction loadings. An elongated member or spreader bar is secured to the spring. A head halter or headstall for fastening to the user's head is mountable to the spreader bar.

According to the invention, the user is quickly and conveniently able to achieve a range of loadings in the operating position or no loading in the rest position by simply moving the headstall fastened to the user's head to different positions.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which.

DESCRIPTION OF THE PREFERRED EMBODIMENT

Figure 1:
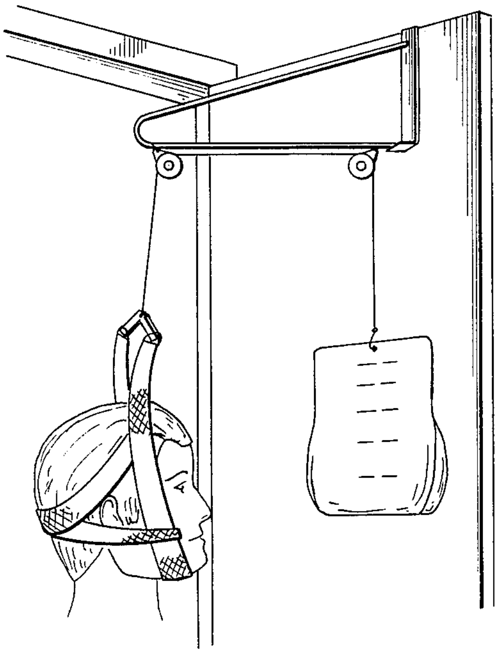
FIG.1 (PRIOR ART)
FIG. 1 is a perspective view of the prior art traction unit installed on a door.

FIG. 1 illustrates the prior art cervical traction unit described in the Description of the Prior Art section.

Figure 4:
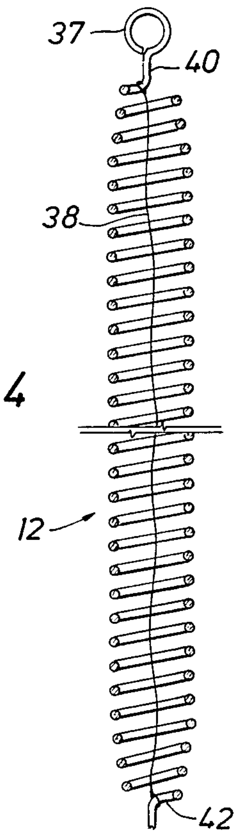
FIG. 4 is an enlarged sectional view of the spring of the present invention in the operating position.
Figure 2:
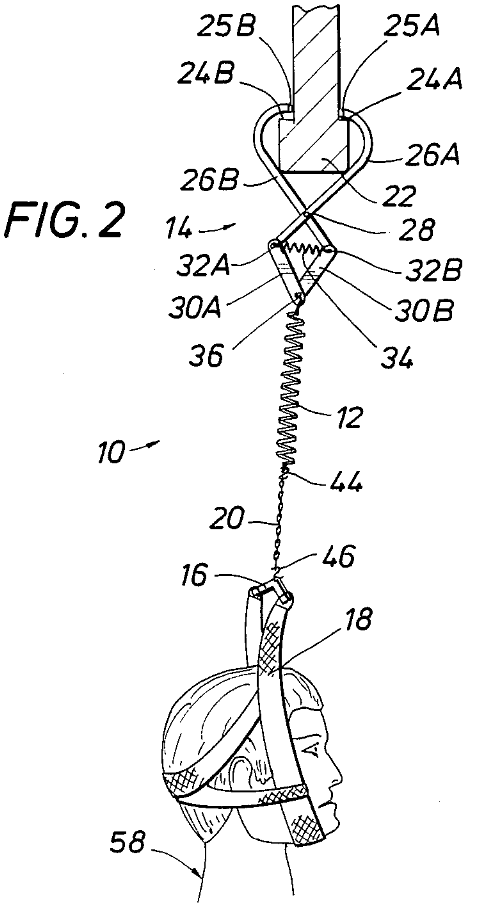
FIG. 2 is a elevational sectional view of the cervical traction unit of the invention in the operating position.
Figure 3:
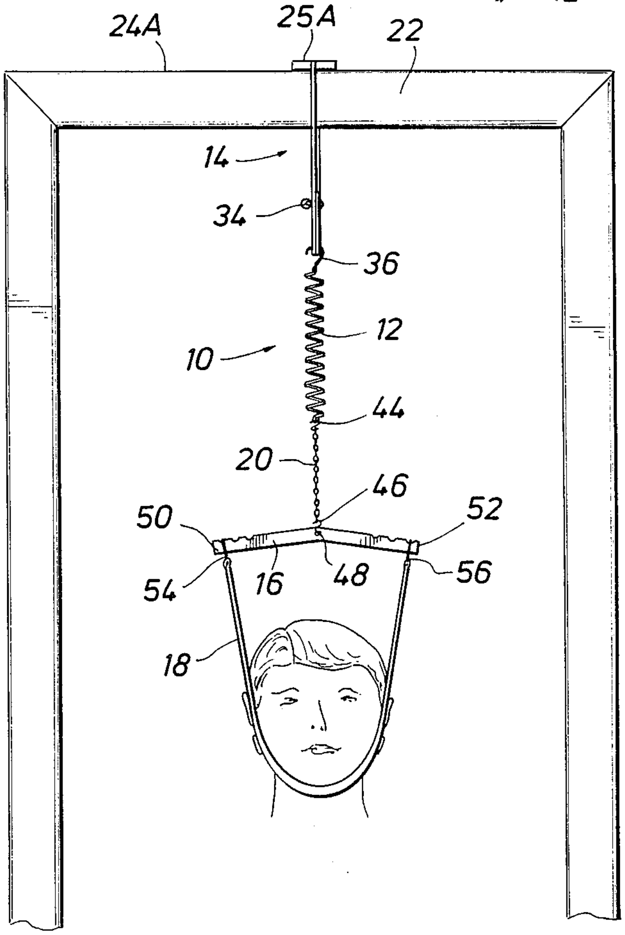
FIG. 3 is a front view of the invention removably secured on an overhead door frame in the operating position.

FIGS. 2–4 illustrate the cervical traction unit of the present invention, generally indicated as 10. The cervical traction unit comprises a spring 12 mounted with a clamp, generally indicated at 14, an elongated member or spreader bar 16 and a headstall or halter 18. Additionally the preferred embodiment includes a chain 20 disposed between the spring 12 and the spreader bar 16 for adjusting a suspended length of the headstall as desired by the user.

The clamp 14 is removably securable to an overhead fixed door frame 22 having projecting shoulders 24A and 24B. The preferred clamp includes curved scissor-type arms or members 26A and 26B pivotable about pin 28, as best shown in FIG. 2. Members or links 30A and 30B are pivotably joined at their upper ends by pins 32A and 32B to the lower extending ends of respective curved members 26A and 26B. Spring 34 is secured to pin 32A and pin 32B to aid in the securement of clamp 14 urging the upper ends 25A and 25B of members 26A and 26B toward each other over shoulders 24A and 24B.

A heavy gauge S hook 36 is received through aligned apertures in members 30A and 30B. The heavy gauge S hook 36 is preferably connected directly to a ring 37 integral with spring 12 for mounting the spring with the clamp 14. The spring 12 is movable relative to the clamp between a rest position (not shown) and an operating position as shown in FIGS. 2–4 for providing a range of loadings.

Turning now to FIG. 4, an enlarged sectional elevational view of the spring 12 is illustrated. The spring 12 includes a cord 38 connected to the spring 12 between end 40 and end 42 for preventing further expansion of the spring. The spring is expandable in the operating position until the length of its ends 40 and 42 are equal to the predetermined cord 38 length. The cord 38 is preferably a nylon cord cpable of withstanding a loading in excess of 40 pounds. The use of the cord will be discussed below in detail.

A chain 20 is connected to the spring 12 by a light gauge S hook 44. The other end of the chain 20 is connected to the spreader bar 16 by an identical S hook 46. The chain length is preferably disposed between the spring and the spreader bar for allowing ease of adjustment of the suspended length of the headstall to the clamp when the spring is in the rest or nonloaded position. This chain 20 allows the user of the apparatus to adjust for different heights of chairs or different heights of door frames used when operating the apparatus and for different upper body height of users and to adjust the amount of upward force or traction to be applied to the head. The S hooks 44 and 46 provide a safety means for disengaging the headstall from the clamp upon a predetermined loading. In the preferred embodiment the identical S hooks 44 and 46 are designed to bend and therefore disengage the spreader bar 16 from the spring 12 at approximately 40 pounds of pull to prevent injuries.

The spreader bar 16 is substantially a horizontal bar having an aperture 48 therein for securement to the S hook 46. The bar 16 further has a plurality of upwardly facing notches at a first end 50 and a second end 52 for securement of D hooks 54 and 56, respectively, of the headstall 18.

OPERATION AND USE

In the operation and use of the present invention the user would separate the curved members 26A and 26B of the clamp 14 so that the ends 25A and 25B clear the door frame 22 and are received on the shoulders 24A and 24B. The spring 34 urges the curved members 26A and 26B together for providing a removably securable clamp 14. The clamp 14, illustrated in FIGS. 2 and 3, is preferred as it provides additional clamping securement of the apparatus to the door frame when the spring 12 is in the operating position. The additional loading on the clamp 14 by spring 12 draws pins 32A and 32B of member 30A and 30B together to further aide the urging of spring 34. Therefore the ends 25A and 25B of members 26A and 26B are urged together to assure a secure clamping of the apparatus. Desirably, this additional clamping force is achieved when most required; in the operating position of the apparatus.

The spring 12 is then suspended from the clamp 14 by a heavy gauge S hook 36 as previously described. The user then fastens the headstall 18 to his or her head, as shown in FIGS. 2 and 3, and secure the D hooks 54 and 56 to the desired notch on the ends 50 and 52 of the spreader bar 16. The notches in the spreader bar are used to adapt the headstall for small to large heads.

If the user finds that the suspended length of the headstall is not of a desired length to achieve desired traction force, a length of chain 20 may be connected between the spring 12 and the spreader bar 16 to achieve the desired length and traction force. Adjusting the chain length 20 by means of hook 44 to the lower end of spring 12 (and/or hook 46 to spreader bar 16) allows the user to adjust the effective length of chain 20 between spring 12 and spreader bar 16 in order to achieve a desired traction loading on his head. If only a small amount of traction force is desired, for example, hook 44 is connected to one of the lengths of chain 20 near its upper end so that spring 12 is relatively extended only a small distance when the user is sitting in a chair beneath door frame 22. If a larger amount of traction force is desired, the chain 20 is shortened between spreader bar 20 and the lower end of spring 20 by connecting hook 44 (and/or hook 46) to one of the intermediate links of chain 20. Providing an adjustable length chain 20 results in a simple, yet effective, means for the user to adjust the upward force of the spring to the headstall 18. It is important to note that even if the chain 20 is not required that a single S hook 44 or 46 would be used to safely connect the spring 12 to the bar 16. When the desired length is achieved the user will sit on a chair positioned near the door frame 22. Simultaneously, the user's head is positioned laterally with respect to the plane of the doorframe to operably move the spring 12 to the operating position to provide a desired traction loading to the user. For a given legnth of chain 20 between spring 12 and spreader bar 16, the user way adjust the traction force on his head by moving his chair laterally backward with respect to doorframe 22, thereby increasing the extension of spring 12 and its upward force on the head through headstall 18.

It has been found that a vector is required in order to provide the proper loading to the cervical spine area of the user, as generally indicated at 58 in FIG. 2. The novel securement of the present invention to a door frame instead of a door allows the user to achieve this vector while providing enhanced horizontal viewing to the user for watching children or television.

The present invention also includes a means for indicating to the user a predetermined loading of the spring 12 in the operating position, as best shown in FIG. 4. The cord 38 is presized in length at the factory so that when the spring is expanded to the cord length, a loading of approximately 15 pounds is provided. Fifteen (15) pounds is selected since it is approximately the average weight of a human head.

Therefore the user may operate the apparatus quickly and conveniently by positioning of the headstall fastened to his or her head. This positioning provides a range of traction loadings between 0, when the spring is in the rest position, to 15 pounds or any desired weight selected when the spring is in the operating position.

A novel and unobvious compact and inexpensive cervical traction unit is therefore disclosed which provides ease in installation and convenience of use to the user. The novel placement of the cervical traction unit allows for increased viewing to the user. More importantly, the user is able to achieve a range of loadings in the operating position, quickly and conveniently, by positioning of the headstall fastened to the user's head. This is highly desirable as it eliminates the inconvenience of draining and filling water to the prior art water bag.

Additionally, the present cervical traction unit is compact to allow its portable use in travelling by user. The user is able to use the traction unit when away from home.

Various modifications and alterations in the disclosed apparatus and methods will be apparent to those skilled in the art of the foregoing description which does not depart from the spirit of the invention. For this reason, these changes are desired to be included in the appended claims. The appended claims recite only the limitation to the present invention in the description manner which is employed for setting forth the embodiments and is to be interpreted as illustrative and not limitative.

What is claimed is:

1. In combination with a door frame defining a doorway and having a fixed overhead frame portion including opposed projecting shoulders;

an improved cervical traction apparatus comprising:

a pair of pivotally connected scissor arms having extending opposed upper ends fitting over said projecting shoulders for supporting said apparatus in a vertically suspended relation and having extending opposed lower ends;

a pair of links having lower ends pivotally connected to each other and having upper ends pivotally connected to said opposed lower ends of said scissor arms;

spring means extending between said opposed lower ends of said scissor arms and between the upper ends of said links for continuously urging said upper ends of said scissor arms toward each other for gripping said projecting shoulders;

a headstall adapted to be worn about the head of a patient seated on a chair within the doorway;

a tension spring having opposed upper and lower ends with said upper end supported from said lower end of said links;

an adjustable length chain connected between said lower end of said spring and said headstall whereby said patient may operably adjust the amount of traction applied to said headstall by adjusting the length of said chain, said amount of traction applied to said headstall being increased for a predetermined length of chain upon lateral movement of the patient and chain laterally away from the doorway; and means connected between the upper and lower ends of said spring to limit the expansion of said tension spring to a predetermined amount.

2. In combination with a door frame defining a doorway and a fixed overhead door frame portion including opposed projecting shoulders;

cervical traction apparatus suspended vertically from said fixed overhead door frame portion;

said apparatus comprising a pair of pivotally connected scissor arms having extending opposed upper ends fitting over said projecting shoulders for supporting said apparatus in a vertically suspended relation and having extending opposed lower ends;

spring means extending between said opposed lower ends of said scissor arms for continuously urging said upper ends toward each other for gripping said projecting shoulders;

a headstall adapted to be worn about the head of a patient seated on a chair within the doorway;

a tension spring having opposed upper and lower ends with its upper end supported from said lower end of said scissor arms;

an adjustable length chain connected between said lower end of said spring and said headstall whereby said patient may operably adjust the amount of traction applied to said headstall by adjusting the length of said chain, said amount of traction applied to said headstall being increased for a predetermined length of chain upon lateral movement of the patient and chair laterally away from the doorway; and a cord of predetermined length connected between the upper and lower ends of said tension spring within the interior of said spring, the length of the cord operably preventing extension of said spring beyond said length.

3. The combination as set forth in claim 2 wherein a pair of links pivotally mounted to each other at their lower ends are pivotally mounted at their upper ends to said opposed lower ends of said scissor arms and said spring means extend between and are connected to the upper ends of said links, said tension spring being supported from the lower ends of said links.

* * * * *